United States Patent
Kosumi et al.

(10) Patent No.: US 8,664,420 B2
(45) Date of Patent: Mar. 4, 2014

(54) PROCESS FOR PRODUCTION OF ZINC TOLUENESULFONATE, ZINC TOLUENESULFONATE, AND PROCESS FOR PRODUCTION OF CARBAMATE

(75) Inventors: Kazuhiro Kosumi, Omuta (JP); Takeshi Fukuda, Kurume (JP); Masaaki Sasaki, Ichihara (JP)

(73) Assignee: Mitsui Chemicals, Inc., Tokyo (JP)

( * ) Notice: Subject to any disclaimer, the term of this patent is extended or adjusted under 35 U.S.C. 154(b) by 0 days.

(21) Appl. No.: 13/517,022

(22) PCT Filed: Jan. 7, 2011

(86) PCT No.: PCT/JP2011/050140
§ 371 (c)(1),
(2), (4) Date: Jun. 18, 2012

(87) PCT Pub. No.: WO2011/089932
PCT Pub. Date: Jul. 28, 2011

(65) Prior Publication Data
US 2012/0259134 A1  Oct. 11, 2012

(30) Foreign Application Priority Data

Jan. 22, 2010 (JP) .................. 2010-012585

(51) Int. Cl.
*C07F 3/06* (2006.01)
*C07C 269/00* (2006.01)

(52) U.S. Cl.
USPC .......................... 556/119; 560/157

(58) Field of Classification Search
USPC .......................... 556/119; 560/157
See application file for complete search history.

(56) References Cited

U.S. PATENT DOCUMENTS 5,698,731 A    12/1997    Bosetti et al.

FOREIGN PATENT DOCUMENTS

| CN | 1939951 A    | 4/2007 |
|----|--------------|--------|
| EP | 2 412 703 A1 | 2/2012 |
| JP | 04-139159    | 5/1992 |
| JP | 9-100265     | 4/1997 |
| JP | 2007-021435  | 2/2007 |

OTHER PUBLICATIONS

International Search Report PCT/JP2011/050140 dated Apr. 12, 2011.
L.-H. Zhang et al., "Characteristics of Thermal Decomposition Products of Rare Earth, Alkali Earth Metal and Transition Metal *p*-Toluenesulfonates", Journal of Thermal Analysis and Calorimetry, vol. 79 (2005) pp. 731-735.
Mercedes Bombin et al., "Thermal Decomposition of Co(II), Ni(II), Cu(II), Zn(II), Cd(II), and Pb(II) *p*-Toluenesulphonates", Thermochimica Acta, 146 (1989) pp. 341-352.
Supplementary European Search Report EP Application No. 11734539.7 dated Jun. 28, 2013.
Kenneth R. Adam et al., "Structure-Function Relationships in the Interaction of Zinc(II) and Cadmium(II) with an Extended Range of 16- to 19-Membered Macrocycles Incorporating Oxygen, Nitrogen, and Sulfur Donor Atoms", Inorg. Chem. 1994, 33, 1194-1200.
Robert G. Salomon et al., "Total Synthesis of Spatol and Other Spatane Diterpenes", J. Am. Chem. Soc., 1991, 113, 3096-3106.
Qing Wang et al., "Syntheses and Crystal Structures of Linear and Zig-zag 1D Coordination Polymers with Schiff-base N,N'-Type Ligands", Z. Anorg. Allg. Chem. 2007, 633, 2463-2469.

*Primary Examiner* — Porfirio Nazario Gonzalez
(74) *Attorney, Agent, or Firm* — Foley & Lardner LLP

(57) ABSTRACT

A process for producing zinc toluenesulfonate comprising reacting a zinc compound comprising $Zn(OH)_2$ with toluenesulfonic acid and/or a salt thereof in the presence of an alcohol having 1 to 20 carbon atoms in total at a temperature higher than 60° C.

5 Claims, No Drawings

PROCESS FOR PRODUCTION OF ZINC TOLUENESULFONATE, ZINC TOLUENESULFONATE, AND PROCESS FOR PRODUCTION OF CARBAMATE

TECHNICAL FIELD

The present invention relates to a process for producing zinc toluenesulfonate, zinc toluenesulfonate, and a process for producing carbamates. More particularly, the present invention relates to a process for producing zinc toluenesulfonate, zinc toluenesulfonate obtained by the process, and a process for producing carbamates using the zinc toluenesulfonate.

BACKGROUND ART

Zinc toluenesulfonate is widely used as a catalyst in various chemical reactions such as a reaction in which carbamates are produced from amine, urea and/or N-unsubstituted carbamate, and alcohol; a reaction in which a polyimide compound is obtained by dehydration condensation of amino acid; and a reaction in which an amide compound is produced from carboxylic acids and amines.

Such zinc toluenesulfonate is produced, for example, by allowing $ZnCO_3$ (zinc carbonate) and para-toluenesulfonic acid to react in water at room temperature, subsequently stirring and filtering the reaction mixture at room temperature, and recrystallizing the obtained filter residue (see, for example, the following Non Patent Document 1).

CITATION LIST

Non-Patent Document 1: Thermochimica Acta: vol. 146 (1989) p. 341-352

DISCLOSURE OF THE INVENTION

Problems to be Solved

However, $ZnCO_3$ (zinc carbonate) used for the process described in Non-Patent Document 1 is expensive, failing to provide cost advantages. Therefore, there remains a need for a process which can industrially produce zinc toluenesulfonate at low cost.

It is an object of the present invention to provide a process for producing zinc toluenesulfonate which can produce zinc toluenesulfonate at low cost, zinc toluenesulfonate obtained by the process, and a process for producing carbamates using the zinc toluenesulfonate.

Means for Solving the Problem

The process for producing zinc toluenesulfonate according to the present invention includes allowing a zinc compound containing $Zn(OH)_2$, and toluenesulfonic acid and/or a salt thereof to react at a temperature higher than 60° C. in the presence of an alcohol having 1 to 20 total carbon atoms.

The zinc toluenesulfonate of the present invention is produced by the above-mentioned process for producing zinc toluenesulfonate.

It is preferable that the zinc toluenesulfonate of the present invention contains 70 parts by mass or more of zinc toluenesulfonate zerohydrate in 100 parts by mass of a total amount of zerohydrate to hexahydrate of zinc toluenesulfonate.

The zinc toluenesulfonate of the present invention contains alcohol in a proportion of not less than 5 ppm to a total amount of zerohydrate to hexahydrate of zinc toluenesulfonate.

It is preferable that the zinc toluenesulfonate of the present invention is used as a catalyst in production of carbamates in which aromatic diamine, urea and/or N-unsubstituted carbamate, and alcohol are allowed to react.

The process for producing carbamates according to the present invention includes allowing aromatic diamine, urea and/or N-unsubstituted carbamate, and alcohol to react in the presence of a catalyst containing the above-mentioned zinc toluenesulfonate.

Effect of the Invention

According to the process for producing zinc toluenesulfonate of the present invention, a zinc compound containing $Zn(OH)_2$ is used as a raw material component, so that zinc toluenesulfonate can be industrially produced at low cost.

Therefore, the zinc toluenesulfonate of the present invention can be obtained at low cost.

Further, according to the process for producing carbamates of the present invention, the above-mentioned zinc toluenesulfonate obtained at low cost is used as a catalyst, so that carbamates can be produced at low cost.

EMBODIMENT OF THE INVENTION

The process for producing zinc toluenesulfonate according to the present invention allows a zinc compound to react with toluenesulfonic acid and/or a salt thereof. In the present invention, the zinc compound contains $Zn(OH)_2$ (zinc hydroxide) as an essential component.

$Zn(OH)_2$ is a hydroxide of zinc and is classified into, for example, α type, β type, γ type, δ type, and ε type depending on its crystal structure.

These types of $Zn(OH)_2$ can be used alone or in combination of two or more kinds.

The $Zn(OH)_2$ is not particularly limited and can be produced by a known process such as by adding alkali hydroxide (NaOH, etc.) to an aqueous zinc salt solution containing $Zn^{2+}$ (zinc ion).

Commercially available $Zn(OH)_2$ may be used as an industrial raw material.

In the present invention, the zinc compound contains at least $Zn(OH)_2$ and may also contain, for example, $ZnCO_3$ (zinc carbonate) as an optional component.

Examples of the zinc compound containing $Zn(OH)_2$ and $ZnCO_3$ include basic zinc carbonate.

The basic zinc carbonate can be obtained as an industrial raw material inexpensively and easily, so that the use of the basic zinc carbonate allows zinc toluenesulfonate to be effectively produced industrially at low cost.

The basic zinc carbonate contains $ZnCO_3$ and $Zn(OH)_2$ as a mixture thereof or a double salt and is represented, for example, by the following general formula (1):

$$a ZnCO_3 \cdot b Zn(OH)_2 \qquad (1)$$

(wherein a represents a composition ratios of $ZnCO_3$ and b represents a composition ratio of $Zn(OH)_2$.)

In general formula (1) above, in the case of setting a to 1, the composition ratio of $Zn(OH)_2$ is, for example, from 0.1 to 50, preferably from 0.5 to 20, or more preferably from 1 to 10.

The basic zinc carbonate contains Zn (zinc) in an amount of, for example, 53 to 66 parts by weight per 100 parts by mass of the basic zinc carbonate. When the Zn is converted into ZnO (zinc oxide), the content of ZnO (zinc oxide) is in the range of, for example, 66 to 82 parts by weight per 100 parts by mass of the basic zinc carbonate.

The basic zinc carbonate may contain water of hydration.

In such a case, the hydrate of the basic zinc carbonate is represented, for example, by the following general formula (2):

$$a ZnCO_3 \cdot b Zn(OH)_2 \cdot c H_2O \qquad (2)$$

(wherein a is as defined for a in formula (1) above, b is as defined for b in formula (1) above, and c represents a composition ratio of $H_2O$.)

In the general formula (2) above, the $H_2O$ composition ratio represented by c is, for example, from 0.1 to 10, preferably from 0.5 to 7, or more preferably from 0.3 to 5.

The basic zinc carbonate may contain various impurities (components other than $ZnCO_3$, $Zn(OH)_2$, and $H_2O$) such as Pb (lead), Cd (cadmium), and As (arsenic).

When the basic zinc carbonate contains impurities, the content of the (total) impurities is, for example, 5 parts by mass or less, or preferably 3 parts by mass or less, per 100 parts by mass of the basic zinc carbonate.

Such basic zinc carbonate can be produced by a known process such as by allowing a zinc salt solution and sodium carbonate to react.

As the basic zinc carbonate, commercially available products used as industrial raw materials such as a raw material of zinc oxide or a raw material for surface treatment of steel plates may be used.

The toluenesulfonic acid and/or its salt is/are any one of toluenesulfonic acid, a toluenesulfonic acid salt, and a mixture of toluenesulfonic acid and a toluenesulfonic acid salt. The toluenesulfonic acid salt is a salt of toluenesulfonic acid and a known salt may be used.

The toluenesulfonic acid is represented, for example, by the following formula (3):

$$CH_3C_6H_4-SO_3H \qquad (3)$$

More specifically, examples of the toluenesulfonic acid include ortho-toluenesulfonic acid (an embodiment in which $CH_3C_6H_4-$ is an ortho-methylphenyl group in formula (3) above), meta-toluenesulfonic acid (an embodiment in which $CH_3C_6H_4-$ is a meta-methylphenyl group in formula (3) above), para-toluenesulfonic acid (an embodiment in which $CH_3C_6H_4-$ is a para-methylphenyl group in formula (3) above).

These toluenesulfonic acids can be used alone or in combination of two or more kinds.

As the toluenesulfonic acid, para-toluenesulfonic acid is preferable.

When para-toluenesulfonic acid is used as the toluenesulfonic acid, the zinc toluenesulfonate can provide a better performance as a catalyst in the production of carbamates to be described later.

The toluenesulfonic acid may contain water of hydration.

In such a case, the hydrate of the toluenesulfonic acid is represented, for example, by the following general formula (4):

$$CH_3C_6H_4-SO_3H \cdot d H_2O \qquad (4)$$

(wherein d represents a composition ratio of $H_2O$.)

In the general formula (4) above, the $H_2O$ composition ratio represented by d is, for example, from 0.8 to 1.2, preferably from 0.9 to 1.1, or more preferably 1.

Such toluenesulfonic acid and/or its salt can be produced by a known process. Commercially available toluenesulfonic acid and/or its salt used as a raw material for organic synthesis, etc may be used.

These toluenesulfonic acids and/or salts thereof can be used alone or in combination of two or more kinds.

In the reaction of the zinc compound with the toluenesulfonic acid and/or its salt, the blending proportion (the number of moles) of the toluenesulfonic acid and/or its salt is in the range of, for example, 0.1 to 10 mol, preferably 0.3 to 5 mol, or more preferably 0.5 to 3 mol, per 1 mol of the zinc compound, and is in the range of, for example, 0.1 to 10 mol, preferably 0.3 to 5 mol, or more preferably 0.5 to 3 mol, per 1 mol of Zn (zinc) contained in the zinc compound.

In this process, the zinc compound, and the toluenesulfonic acid and/or its salt are allowed to react in the presence of alcohol having 1 to 20 total carbon atoms as a solvent.

Examples of the alcohol having 1 to 20 total carbon atoms include monohydric alcohol having 1 to 20 total carbon atoms, dihydric alcohol having 1 to 20 total carbon atoms, and trihydric alcohol having 1 to 20 total carbon atoms.

Examples of the monohydric alcohol having 1 to 20 total carbon atoms include aliphatic monohydric alcohols such as methanol, ethanol, propanol, iso-propanol, butanol (1-butanol), iso-butanol, sec-butanol, tert-butanol, pentanol, iso-pentanol, sec-pentanol, hexanol, heptanol, octanol, 2-ethylhexanol, nonanol, decanol, isodecanol, dodecanol, tetradecanol, hexadecanol, octadecanol, and eicosanol; and aromatic monohydric alcohols such as phenol, hydroxytoluene, hydroxyxylene, biphenyl alcohol, naphthalenol, anthracenol, and phenanthrenol.

In addition, examples thereof further include ethylene glycol monoalkyl ethers such as ethylene glycol monomethyl ether(methyl cellosolve), ethylene glycol monoethyl ether (ethyl cellosolve), ethylene glycol monoisopropyl ether, ethylene glycol monobutyl ether(butyl cellosolve), and ethylene glycol monohexyl ether; diethylene glycol monoalkyl ethers such as diethylene glycol monomethyl ether(methyl carbitol), diethylene glycol monoethyl ether(ethyl carbitol), and diethylene glycol monobutyl ether(butyl carbitol); dipropylene glycol monoalkyl ethers such as dipropylene glycol monomethyl ether and dipropylene glycol monoethyl ether; triethylene glycol monomethyl ether, triethylene glycol monoethyl ether, and glycerol dialkyl ether.

Examples of the dihydric alcohol having 1 to 20 total carbon atoms include ethylene glycol, propylene glycol, 1,4-butylene glycol, 1,3-butylene glycol, 1,2-butylene glycol, 2-methyl-1,3-propanediol, 1,5-pentanediol, neopentyl glycol, 3-methyl-1,5-pentanediol, 2,4-diethyl-1,5-pentanediol, 1,6-hex and iol, 2,6-dimethyl-1-octene-3,8-diol, alkane (of 7 to 20 carbon atoms) diol, cyclohexane dimethanol, hydrogenated bisphenol-A, 1,4-dihydroxy-2-butene, bishydroxyethoxy benzene, xylene glycol, bishydroxyethylene terephthalate, bisphenol A, diethylene glycol, trioxyethylene glycol, tetraoxyethylene glycol, pentaoxyethylene glycol, hexaoxyethylene glycol, dipropylene glycol, trioxypropylene glycol, tetraoxypropylene glycol, pentaoxypropylene glycol, and hexaoxypropylene glycol.

Examples of the trihydric alcohol having 1 to 20 total carbon atoms include glycerol, 2-methyl-2-hydroxymethyl-1,3-propanediol, 2,4-dihydroxy-3-hydroxymethylpentane, 1,2,6-hexanetriol, trimethylolpropane, 2,2-bis(hydroxymethyl)-3-butanol, and other aliphatic triols (of 8 to 20 carbon atoms).

These alcohols can be used alone or in combination of two or more kinds.

Of these alcohols having 1 to 20 total carbon atoms, alcohol having 2 to 8 total carbon atoms is preferable, or monohydric alcohol having 2 to 8 total carbon atoms is more preferable.

In addition to the above-mentioned alcohols having 1 to 20 total carbon atoms, for example, water or a known organic solvent for industrial use may further be used as a solvent in combination as required.

When the alcohol having 1 to 20 total carbon atoms is adopted, zinc toluenesulfonate having a reduced content of water of hydration, such as a zerohydrate (anhydrate) of zinc toluenesulfonate, can be obtained.

Usually, when zinc toluenesulfonate containing a large amount of water of hydration is used as a catalyst in the production (a reaction in which carbamates are produced from amine, urea and/or N-unsubstituted carbamate, and alcohol) of carbamates to be described later, the water of hydration contained therein may react with the urea and/or the N-unsubstituted carbamate to form an undesirable by-product in some cases. Further, the reaction of the water of hydration with the urea and/or the N-unsubstituted carbamate may lose the urea and/or the N-unsubstituted carbamate, thereby deteriorating the yield of carbamate which is a desired compound in some cases.

In contrast to this, when the zinc toluenesulfonate having a reduced water of hydration content is used as a catalyst, the reaction of the water of hydration of zinc toluenesulfonate with the urea and/or N-unsubstituted carbamate can be reduced, so that the loss of the urea and/or the N-unsubstituted carbamate can be suppressed. As a result, carbamates can be produced efficiently.

On the other hand, in order to obtain the zinc toluenesulfonate having a reduced water of hydration content without resort to the above-mentioned process, it is also studied that, for example, the hydrate of zinc toluenesulfonate is dried to remove the water of hydration. In such a case, however, the hydrate of zinc toluenesulfonate must be heated to high temperature, thereby disadvantageously leading to increase in cost and man-hour.

In contrast, the above-mentioned process can eliminate the need for heating and drying and can also reduce the water of hydration content of the zinc toluenesulfonate. As a result, cost reduction can be achieved.

Of the alcohols having 1 to 20 total carbon atoms, the same kind of alcohol as the alcohol (alcohol used in a reaction of aromatic diamine, urea and/or N-unsubstituted carbamate, and alcohol) used in the production of carbamates to be described later is even more preferable.

When the same kind of alcohol as that used in the production of carbamates is used as a solvent in the production of zinc toluenesulfonate, the obtained zinc toluenesulfonate can be used in the production of carbamates without being isolated or washed.

The blending amount of the solvent is not particularly limited and the solvent can be blended at an appropriate proportion to the zinc compound and the toluenesulfonic acid.

In this reaction, the reaction temperature is higher than 60° C., preferably higher than 70° C., more preferably higher than 90° C., or even more preferably higher than 95° C., and is usually 300° C. or lower.

When the reaction temperature is less than the above-mentioned lower limit, the reaction rate is slow, so that it takes a significant time to obtain zinc toluenesulfonate at a good yield.

On the other hand, when the reaction temperature exceeds the above-mentioned upper limit, a decomposition reaction of the zinc toluenesulfonate occurs, which may deteriorate the yield of the zinc toluenesulfonate.

In this reaction, the reaction time is, for example, for 1 minute or longer, or preferably for 5 minutes or longer.

When the reaction time is less than the above-mentioned lower limit, the yield of the zinc toluenesulfonate may deteriorate.

The reaction is usually carried out under atmospheric pressure. However, when the boiling point of the component in the reaction solution is lower than the reaction temperature, the reaction may be carried out under an increased pressure or, if necessary, under a reduced pressure.

Then, this reaction may be carried out, for example, by charging a zinc compound and a solvent in a reaction vessel under the above-mentioned conditions, and stirring or mixing the charged mixture while by supplying or adding dropwise a solution having a toluenesulfonic acid and/or a salt thereof dissolved in the solvent. Alternatively, this reaction may be carried out, for example, by charging a zinc compound, toluenesulfonic acid and/or a salt thereof, and a solvent by a batch in a reaction vessel, and stirring or mixing the charged mixture.

Thus, a zinc toluenesulfonate corresponding to the above-mentioned toluenesulfonic acid can be produced.

The zinc toluenesulfonate is represented, for example, by the following formula (5):

$$(CH_3C_6H_4-SO_3)_2Zn \qquad (5)$$

More specifically, examples of the zinc toluenesulfonate include zinc ortho-toluenesulfonate (an embodiment in which $CH_3C_6H_4-$ is an ortho-methylphenyl group in formula (5) above), zinc meta-toluenesulfonate (an embodiment in which $CH_3C_6H_4-$ is a meta-methylphenyl group in formula (5) above), and zinc para-toluenesulfonate (an embodiment in which $CH_3C_6H_4-$ is a para-methylphenyl group in formula (5) above).

The zinc toluenesulfonate thus obtained optionally contains water of hydration.

More specifically, when the zinc compound, and the toluenesulfonic acid and/or its salt are allowed to react in the presence of the alcohol having 1 to 20 total carbon atoms as described above, a zerohydrate (anhydrate) of the zinc toluenesulfonate can be obtained and a small amount of hydrate of the zinc toluenesulfonate may generate.

In such a case, the zinc toluenesulfonate hydrate is represented, for example, by the following general formula (6):

$$(CH_3C_6H_4-SO_3)_2Zn \cdot eH_2O \qquad (6)$$

(wherein e represents a composition ratio of $H_2O$.)

In the general formula (6) above, the average composition ratio of $H_2O$ represented by e is, for example, higher than 0 and 6 or less, preferably 4 or less, or more preferably 2 or less.

That is, in this process, the zinc toluenesulfonate is usually obtained as zerohydrate to hexahydrate.

In the case where the water of hydration content (the number of moles) of the zinc toluenesulfonate exceeds the above-mentioned upper limit, the use of the zinc toluenesulfonate as a catalyst in the reaction in which carbamates are produced from amine, urea and/or N-unsubstituted carbamate, and alcohol allows the water of hydration to react with the urea and/or the N-unsubstituted carbamate, which may in turn lose the urea and/or the N-unsubstituted carbamate which is/are raw material component(s).

In the case where the zinc toluenesulfonate contains a zerohydrate (anhydrate) of zinc toluenesulfonate and a hydrate (e.g., hexahydrate) of zinc toluenesulfonate, the content ratio of the zerohydrate (on a mass basis) is in the range of preferably 70 parts by mass or more, or more preferably 80 parts by mass or more, per 100 parts by mass of the total amount of the zerohydrate and the hydrate.

When the content ratio of the above-mentioned zerohydrate in the zinc toluenesulfonate is within the above range, the loss of the urea and/or the N-unsubstituted carbamate can be reduced even when the zinc toluenesulfonate is used as a catalyst in the reaction in which carbamates are produced from amine, urea and/or N-unsubstituted carbamate, and alcohol.

To purify the zinc toluenesulfonate thus obtained, the zinc toluenesulfonate is separated from the reaction solution containing, for example, excess (unreacted) zinc compound and/or toluenesulfonic acid and/or a salt thereof, and further a solvent, and optionally containing a by-product by a known separation process such as filtration. Subsequently, the separated solution including the zinc toluenesulfonate is heated and depressurized as required.

Since an alcohol is used as a solvent, the zinc toluenesulfonate thus obtained contains the alcohol in a proportion of, for example, 5 ppm or more, or preferably 1 ppm or more, to the total amount of zerohydrate to hexahydrate of the zinc toluenesulfonate.

The yield of the zinc toluenesulfonate (containing water of hydration) is, for example, 85% by mol or more, or preferably 90% by mol or more, based on the toluenesulfonic acid and/or its salt According to the process for producing the zinc toluenesulfonate, a zinc compound containing $Zn(OH)_2$ is used as a raw material component, so that zinc toluenesulfonate can be industrially produced at low cost.

Therefore, the zinc toluenesulfonate can be obtained at low cost.

For that reason, the zinc toluenesulfonate can be suitably used as a catalyst in the production of carbamates in which aromatic diamine, urea and/or N-unsubstituted carbamate, and alcohol are allowed to react.

The present invention includes a process for producing carbamates in which aromatic diamine, urea and/or N-unsubstituted carbamate, and alcohol are allowed to react in the presence of a catalyst containing the above-mentioned zinc toluenesulfonate.

The aromatic diamine is represented, for example, by the following general formula (7):

$$R^1—(NH_2)_2 \quad (7)$$

(wherein $R^1$ represents an aromatic ring-containing hydrocarbon group having 6 to 15 total carbon atoms.)

In $R^1$, examples of the aromatic ring-containing hydrocarbon group having 6 to 15 total carbon atoms include monovalent to hexavalent aromatic ring-containing hydrocarbon groups having 6 to 15 total carbon atoms.

The aromatic ring-containing hydrocarbon group contains at least one aromatic hydrocarbon in the hydrocarbon group and, for example, an aliphatic hydrocarbon group or the like may be attached to the aromatic hydrocarbon.

More specifically, examples of the aromatic diamine include aromatic primary diamines such as 2,4-tolylenediamine(2,4-diaminotluene), 2,6-tolylenediamine(2,6-diaminotoluene), 4,4'-diphenylmethanediamine, 2,4'-diphenylmethanediamine, 2,2'-diphenylmethanediamine, 4,4'-diphenyletherdiamine, 2-nitrodiphenyl-4,4'-diamine, 2,2'-diphenylpropane-4,4'-diamine, 3,3'-dimethyldiphenylmethane-4,4'-diamine, 4,4'-diphenylpropanediamine, m-phenylenediamine, p-phenylenediamine, naphthylene-1,4-diamine, naphthylene-1,5-diamine, and 3,3'-dimethoxydiphenyl-4,4'-diamine.

These aromatic diamines can be used alone or in combination of two or more kinds.

The N-unsubstituted carbamate used in the present invention is a carbamic acid ester in which a nitrogen atom in a carbamoyl group is not substituted with a functional group (i.e., a nitrogen atom is bonded to two hydrogen atoms and to one carbon atom), and is represented, for example, by the following general formula (8):

$$R^2O—CO—NH_2 \quad (8)$$

(wherein $R^2$ represents an aliphatic hydrocarbon group having 1 to 16 total carbon atoms, or an aromatic hydrocarbon group having 6 to 16 total carbon atoms.)

In formula (8) above, examples of the aliphatic hydrocarbon group having 1 to 16 total carbon atoms represented by $R^2$ include alkyl groups having 1 to 16 total carbon atoms.

Examples of the alkyl group include methyl, ethyl, propyl, iso-propyl, butyl, iso-butyl, sec-butyl, tert-butyl, pentyl, iso-pentyl, sec-pentyl, hexyl, heptyl, octyl, 2-ethylhexyl, nonyl, decyl, isodecyl, dodecyl, tetradecyl, and hexadecyl.

In formula (8) above, examples of the N-unsubstituted carbamate whose $R^2$ is an aliphatic hydrocarbon group having 1 to 16 total carbon atoms include methyl carbamate, ethyl carbamate, propyl carbamate, iso-propyl carbamate, butyl carbamate, iso-butyl carbamate, sec-butyl carbamate, tert-butyl carbamate, pentyl carbamate, iso-pentyl carbamate, sec-pentyl carbamate, hexyl carbamate, heptyl carbamate, octyl carbamate, 2-ethylhexyl carbamate, nonyl carbamate, decyl carbamate, isodecyl carbamate, dodecyl carbamate, tetradecyl carbamate, and hexadecyl carbamate.

In formula (8) above, examples of the aromatic hydrocarbon group having 6 to 16 total carbon atoms represented by $R^2$ include aryl groups having 6 to 16 total carbon atoms.

Examples of the aryl group include phenyl, tolyl, xylyl, biphenyl, naphthyl, anthryl, and phenanthryl.

In formula (8) above, examples of the N-unsubstituted carbamate in which $R^2$ is an aromatic hydrocarbon group having 6 to 16 total carbon atoms include phenyl carbamate, tolyl carbamate, xylyl carbamate, biphenyl carbamate, naphthyl carbamate, anthryl carbamate, and phenanthryl carbamate.

These N-unsubstituted carbamates can be used alone or in combination of two or more kinds.

As the N-unsubstituted carbamate, in formula (8) above, an N-unsubstituted carbamate in which $R^2$ is an aliphatic hydrocarbon group having 1 to 16 total carbon atoms is preferable, or an N-unsubstituted carbamate in which $R^2$ is an aliphatic hydrocarbon group having 2 to 12 total carbon atoms are more preferable.

The alcohol used in the present invention is, for example, a primary to tertiary monohydric alcohol and is represented, for example, by the following formula (9):

$$R^3—OH \quad (9)$$

(wherein $R^3$ represents an aliphatic hydrocarbon group having 1 to 16 total carbon atoms, or an aromatic hydrocarbon group having 6 to 16 total carbon atoms.)

In formula (9) above, examples of the aliphatic hydrocarbon group having 1 to 16 total carbon atoms represented by $R^3$ include the alkyl groups mentioned above.

In formula (9) above, examples of the alcohol in which $R^3$ is an aliphatic hydrocarbon group having 1 to 16 total carbon atoms include methanol, ethanol, propanol, iso-propanol, butanol, iso-butanol, sec-butanol, tert-butanol, pentanol, iso-pentanol, sec-pentanol, hexanol, heptanol, octanol (1-octanol), 2-ethylhexanol, nonanol, decanol, isodecanol, dodecanol, tetradecanol, and hexadecanol.

In formula (9) above, examples of the aromatic hydrocarbon group having 6 to 16 total carbon atoms represented by $R^3$ include the aryl groups mentioned above.

In formula (9) above, examples of the alcohol in which $R^3$ is an aromatic hydrocarbon group having 6 to 16 total carbon atoms include phenol, hydroxytoluene, hydroxyxylene, biphenyl alcohol, naphthalenol, anthracenol, and phenanthrenol.

These alcohols can be used alone or in combination of two or more kinds.

As the alcohol, in formula (9) above, an alcohol in which $R^3$ is an aliphatic hydrocarbon group having 1 to 16 carbon atoms is preferable, or an alcohol in which $R^3$ is an aliphatic hydrocarbon group having 2 to 12 carbon atoms is more preferable.

Further, a primary monohydric alcohol is preferable as the alcohol.

Further, the same kind of alcohol as that contained in the solvent in the production of zinc toluenesulfonate is preferable as the alcohol.

In the process for producing carbamates, the catalyst contains at least the zinc toluenesulfonate mentioned above and may also contain other catalysts as required.

Examples of the other catalyst blended with the zinc toluenesulfonate include compounds of a metal belonging to Group 1 of the Periodic Table (according to the IUPAC Periodic Table of the Elements (version date 22 Jun. 2007); the same applies to the following) (e.g., lithium methanolate, lithium ethanolate, lithium propanolate, lithium butanolate, sodium methanolate, and potassium-tent-butanolate), Group 2 metal compounds (e.g., magnesium methanolate and calcium methanolate), Group 3 metal compounds (e.g., cerium (IV) oxide and uranyl acetate), Group 4 metal compounds (titanium tetraisopropanolate, titanium tetrabutanolate, titanium tetrachloride, titanium tetraphenolate, and titanium naphthenate), Group 5 metal compounds (e.g., vanadium(III) chloride and vanadium acetylacetonato), Group 6 metal compounds (e.g., chromium(III) chloride, molybdenum(VI) oxide molybdenum acetylacetonato, and tungsten(VI) oxide), Group 7 metal compounds (e.g., manganese(II) chloride, manganese(II) acetate, and manganese(III) acetate), Group 8 metal compounds (e.g., iron(II) acetate, iron(III) acetate, iron phosphate, ferrous oxalate, iron(III) chloride, and iron(III) bromide), Group 9 metal compounds (e.g., cobalt acetate, cobalt chloride, cobalt sulfate, and cobalt naphthenate), Group 10 metal compounds (e.g., nickel chloride, nickel acetate, and nickel naphthenate), Group 11 metal compounds (e.g., copper(II) acetate, copper(II) sulfate, copper(II) nitrate, bis-(triphenyl-phosphineoxide)-copper(II) chloride, copper molybdate, silver acetate, and gold acetate), Group 12 metal compounds (e.g., zinc oxide, zinc chloride, zinc acetate, zinc acetonyl acetate, zinc octanoate, zinc oxalate, zinc hexylate, zinc benzoate, and zinc undecylate), Group 13 metal compounds (e.g., aluminium acetylacetonato, aluminium-isobutyrate, and aluminum trichloride), Group 14 metal compounds (e.g., tin(II) chloride, tin(IV) chloride, lead acetate, and lead phosphate), and Group 15 metal compounds (e.g., antimony(III) chloride, antimony(V) chloride, and bismuth(III) chloride).

Further, examples of the other catalyst include $Zn(OSO_2CF_3)_2$ (also known as $Zn(OTf)_2$, zinc trifluoromethanesulfonate), $Zn(OSO_2C_2F_5)_2$, $Zn(OSO_2C_3F_7)_2$, $Zn(OSO_2C_4F_9)_2$, $Zn(OSO_2C_6H_5)_2$, $Zn(BF_4)_2$, $Zn(PF_6)_2$, $Hf(OTf)_4$ (hafnium trifluoromethanesulfonate), $Sn(OTf)_2$, $Al(OTf)_3$, and $Cu(OTf)_2$.

When the catalyst contains zinc toluenesulfonate and other catalysts, the zinc toluenesulfonate is blended in an amount of, for example, 0.01 to 99.99 parts by mass, or preferably 1 to 99 parts by mass, per a total of 100 parts by mass of the catalyst.

In this process, the aromatic diamine, urea and/or N-unsubstituted carbamate, and alcohol are preferably blended and the mixture is allowed to react in the presence of the above-mentioned catalyst containing zinc toluenesulfonate, preferably in a liquid phase.

The blending proportion of the aromatic diamine, urea and/or N-unsubstituted carbamate, and alcohol are not particularly limited and can be appropriately selected over a relatively wide range.

Usually, the blending amounts of the urea and N-unsubstituted carbamate, and the blending amount of the alcohol may be equimolar or more to the amino group in the aromatic diamine, so that the urea and/or the above-mentioned N-unsubstituted carbamate, and the alcohol themselves can also be used as reaction solvents in this reaction.

When the urea and/or the above-mentioned N-unsubstituted carbamate and the alcohol also serve as the reaction solvents, excess amounts of the urea and/or the above-mentioned N-unsubstituted carbamate and the alcohol are used as required. Large excess amounts thereof, however, increase consumption energy in the separation process after the reaction, which may be unsuitable for industrial production.

Therefore, from the viewpoint of improving the yield of the carbamate, the blending amount(s) of the urea and/or the above-mentioned N-unsubstituted carbamate is/are of the order of 0.5 to 20 times moles, preferably 1 to 10 times moles, or more preferably 1 to 5 times moles with respect to one amino group of the aromatic diamine, and the blending amount of the alcohol is of the order of 0.5 to 100 times moles, preferably 1 to 20 times moles, or more preferably 1 to 10 times moles, with respect to one amino group of the aromatic diamine.

The blending amount of the catalyst is in the range of, for example, 0.000001 to 0.1 mol, or preferably 0.00005 to 0.05 mol, per 1 mol of the aromatic diamine.

Even if the blending amount of the catalyst is more than the above range, no further remarkable reaction enhancing effect is observed, but cost may increase due to an increase in the blending amount thereof. On the other hand, when the blending amount is less than the above range, the reaction enhancing effect may not be obtained.

The process for adding the catalyst is not particularly limited, and the process of each of package addition, continuous addition, and intermittent addition in portions does not affect the reaction activity.

In this reaction, although a reaction solvent is not necessarily required, for example, when reaction raw materials are solid or when a reaction product is deposited, blending of the reaction solvent can improve operability.

Such reaction solvent is not particularly limited as long as it is inert to or has poor reactivity to the aromatic diamine, urea and/or N-unsubstituted carbamate, and alcohol, which are reaction raw materials, and to the carbamate which is a reaction product, and examples thereof include aliphatic hydrocarbons (e.g., hexane, pentane, petroleum ether, ligroin, cyclododecane, and decalins); aromatic hydrocarbons (e.g., benzene, toluene, xylene, ethylbenzene, isopropylbenzene, butylbenzene, cyclohexylbenzene, tetralin, chlorobenzene, o-dichlorobenzene, methylnaphthalene, chloronaphthalene, dibenzyltoluene, triphenylmethane, phenylnaphthalene, biphenyl, diethylbiphenyl, and triethylbiphenyl); ethers (e.g., diethyl ether, diisopropyl ether, dibutyl ether, anisole, diphenyl ether, tetrahydrofuran, ethylene glycol dimethyl ether, ethylene glycol diethyl ether, ethylene glycol dibutyl ether, diethylene glycol dimethyl ether, and diethylene glycol diethyl ether); nitriles (e.g., acetonitrile, propionitrile, adiponitrile, and benzonitrile); aliphatic halogenated hydrocarbons (e.g., methylene chloride, chloroform, 1,2-dichloroethane, 1,2-dichloropropane, and 1,4-dichlorobutane); amides (e.g., dimethylformamide and dimethylacetamide); nitro compounds (e.g., nitromethane and nitrobenzene); N-methyl pyrrolidinone, N,N-dimethylimidazolidinone, and dimethyl sulfoxide.

Among these reaction solvents, aliphatic hydrocarbons and aromatic hydrocarbons are preferably used in consideration of economical efficiency, operability, or the like. These reaction solvents can be used alone or in combination of two or more kinds.

The blending amount of the reaction solvent is not particularly limited as long as it is sufficient amount for the carbamate as a desired product to be dissolved. Industrially, the amount of the reaction solvent is preferably minimized as much as possible in view that since it is necessary to recover the reaction solvent from the reaction solution, the energy consumed for the recovery can be reduced as much as possible, and in view that a large amount of the reaction solvent can decrease substrate concentration on the reaction to slow the reaction rate. More specifically, the amount of the reaction solvent is usually in the range of 0.1 to 500 parts by mass, or preferably 1 to 100 parts by mass, per 1 part by mass of the aromatic diamine.

In this reaction, the reaction temperature is appropriately selected from the range of 100 to 350° C., or preferably 150 to 300° C. When the reaction temperature is lower than this range, the reaction rate may decrease. On the other hand, when it is higher than this range, a side reaction increases, so that the yield of the carbamate as a desired product may be reduced.

The reaction is usually carried out under atmospheric pressure. However, when the boiling point of the component in the reaction solution is lower than the reaction temperature, the reaction may be carried out under an increased pressure or, if necessary, under a reduced pressure.

The reaction time is in the range of, for example, 0.1 to 20 hours, or preferably 0.5 to 10 hours. When the reaction time is shorter than this range, the yield of the carbamate as a desired product may be reduced. On the other hand, when it is longer than this range, the reaction is unsuitable for industrial production.

Then, this reaction may be carried out, for example, by charging an aromatic diamine, a urea and/or an N-unsubstituted carbamate, an alcohol, a catalyst, and if necessary, a reaction solvent, in a reaction vessel under the above-mentioned conditions, and stirring or mixing the charged mixture. This produces carbamate as a desired product represented, for example, by the following general formula (10) under a mild condition at low cost and high yield for a short period of time.

$$(R^3OCONH)_2\text{—}R^1 \tag{10}$$

(wherein $R^1$ is as defined for $R^1$ in formula (7) above and $R^3$ is as defined for $R^3$ in formula (9) above.)

In this reaction, ammonia is secondarily produced.

Further, in this reaction, when an N-unsubstituted carbamate is blended, alcohol represented, for example, by the following general formula (11) is secondarily produced:

$$R^2\text{—}OH \tag{11}$$

(wherein $R^2$ is as defined for $R^2$ in formula (8) above.)

In this reaction, either of a batch reaction process or a continuous reaction process can be adopted.

The reaction is carried out preferably while the secondarily produced ammonia is discharged out of the system. Further, when an N-unsubstituted carbamate is blended, the reaction is carried out while the secondarily produced alcohol is distilled out of the system.

Thus, the production of the carbamate as a desired product can be accelerated to further improve the yield.

When the carbamate thus obtained is isolated, the carbamate may be separated from the reaction solution containing, for example, excess (unreacted) urea and/or N-unsubstituted carbamate, excess (unreacted) alcohol, catalyst, carbamate, reaction solvent, secondarily produced ammonia, and optionally, secondarily produced alcohol, by a known separation and purification process.

In the process for producing carbamates, since the zinc toluenesulfonate obtained at low cost is used as a catalyst, carbamates can be produced at low cost.

Further, as a catalyst in the process for producing carbamates, when the zinc toluenesulfonate having a reduced water of hydration content is used as described above, in the case of allowing aromatic diamine, urea and/or N-unsubstituted carbamate, and alcohol to react, the reaction of the water of hydration of the zinc toluenesulfonate with the urea and/or the N-unsubstituted carbamate can be reduced.

Therefore, the process for producing carbamates can suppress loss of the urea and/or the N-unsubstituted carbamate, resulting in effective production of carbamates.

Isocyanates can be produced by thermally decomposing the carbamates obtained by the above-mentioned process for producing carbamates.

Specifically, in the process for producing isocyanates, the carbamates obtained by the above-mentioned process for producing carbamates are thermally decomposed to produce an isocyanate represented by the following general formula (12) corresponding to the above-mentioned aromatic diamine, $$R^1\text{—}(NCO)_2 \tag{12}$$

(wherein $R^1$ is as defined for $R^1$ in formula (7) above) and an alcohol, which is a secondarily product, represented by the following general formula (13):

$$R^3\text{—}OH \tag{13}$$

(wherein $R^3$ is as defined for $R^3$ in formula (9) above.)

No particular limitation is imposed on the thermal decomposition. Known decomposition methods such as a liquid phase method and a vapor phase method can be used.

In the vapor phase method, the isocyanate and alcohol produced by the thermal decomposition can be separated from a gaseous product mixture by fractional condensation. In the liquid phase method, the isocyanate and alcohol produced by the thermal decomposition can be separated, for example, by distillation or using a solvent and/or inert gas as a support substance.

As the thermal decomposition, a liquid phase method is preferable from the viewpoint of workability.

Since the thermal decomposition reaction of the carbamates in the liquid phase method is a reversible reaction, preferably, to suppress a reverse reaction (i.e., the urethane-forming reaction between the isocyanate represented by general formula (12) above and the alcohol represented by general formula (13) above) to the thermal decomposition reaction, the carbamates are thermally decomposed while the isocyanate represented by general formula (12) above and/or the alcohol represented by general formula (13) above are drawn out of the reaction mixture and then separated.

As the reaction condition of the thermal decomposition reaction, preferable are conditions such that the carbamates can be thermally decomposed in an excellent manner, and the isocyanate (general formula (12) above) and alcohol (general formula (13) above) produced by the thermal decomposition process evaporate, whereby the carbamates and the isocyanate fail to reach equilibrium, and further, a side reaction such as polymerization of isocyanates is suppressed.

As the reaction conditions, more specifically, the thermal decomposition temperature is usually 350° C. or lower, preferably from 80 to 350° C., or more preferably from 100 to 300° C. At the thermal decomposition temperature lower than 80° C., a practical reaction rate may not be obtained. On the other hand, at the thermal decomposition temperature higher than 350° C., an undesired side reaction such as polymerization of isocyanates may occur. It is preferable that the pressure during the thermal decomposition reaction is a pressure for allowing the alcohol produced to be vaporized at the thermal decomposition reaction temperature specified above. For practical use, the pressure is preferably in the range of 0.133 to 90 kPa in terms of equipment and utilities.

Although purified carbamates can be used for the thermal decomposition, excess (unreacted) urea and/or N-unsubstituted carbamate, excess (unreacted) alcohol, catalyst, reaction solvent, secondarily produced ammonia, and a crude material of the carbamate obtained by the recovery and separation from the alcohol, optionally, produced secondarily may be used to continue the thermal decomposition after completion of the above-mentioned reaction (i.e., reaction of the aromatic diamine, the urea and/or the N-unsubstituted carbamate, and the alcohol).

Further, if necessary, a catalyst and an inert solvent may be added. Although the catalyst and the inert solvent vary depending on their kinds, they may be added at any timing of during the above-mentioned reaction, before and after distillation and separation after the reaction, and before and after separation of the carbamates.

As the catalyst used for the thermal decomposition, at least one metal selected from the group consisting of Sn, Sb, Fe, Co, Ni, Cu, Cr, Ti, Pb, Mo, and Mn, or a compound thereof such as oxide, halide, carboxylate, phosphate, and organometallic compound, used for the urethane-forming reaction of an isocyanate and a hydroxyl group is used. Among them, Fe, Sn, Co, Sb, and Mn are preferably used in the thermal decomposition because they exhibit the effect of suppressing the production of secondary product.

Examples of the metallic catalyst of Sn include tin oxide, tin chloride, tin bromide, tin iodide, tin formate, tin acetate, tin oxalate, tin octylate, tin stearate, tin oleate, tin phosphorate, dibutyltin dichloride, dibutyltin dilaurate, and 1,1,3,3-tetrabutyl-1,3-dilauryloxydistannoxane.

Examples of the metallic catalysts of Fe, Co, Sb, and Mn include acetate, benzoate, naphthenate, and acetyl acetonate thereof.

The blending amount of the catalyst is in the range of 0.0001 to 5% by mass, or preferably 0.001 to 1% by mass, per the reaction solution, as a metal or a compound thereof.

The inert solvent is not particularly limited as long as it dissolves at least the carbamate, is inert to the carbamate and the isocyanate, and stable at the thermal decomposition temperature. For efficient thermal decomposition reaction, the inert solvent preferably has a higher boiling point than the isocyanate to be produced. Examples of the inert solvent include esters such as dioctyl phthalate, didecyl phthalate, and didodecyl phthalate; and aromatic hydrocarbons or aliphatic hydrocarbons regularly used as heat transfer medium such as dibenzyltoluene, triphenylmethane, phenylnaphthalene, biphenyl, diethylbiphenyl, and triethylbiphenyl. An blending amount of the inert solvent is in the range of 0.001 to 100 parts by mass, preferably 0.01 to 80 parts by mass, or more preferably 0.1 to 50 parts by mass, per 1 part by mass of the carbamate.

The thermal decomposition reaction can be carried out by a batch reaction process in which the carbamate, the catalyst, and the inert solvent are charged by a batch, or by a continuous reaction process in which the carbamate is charged into the inert solvent containing the catalyst under reduced pressure.

In the thermal decomposition, an isocyanate and an alcohol are produced, and for example, allophanate, amines, urea, carbonate, carbamates, and carbon dioxide may also be produced by a side reaction in some cases. Therefore, if necessary, the isocyanate thus produced is purified by a known process.

In the foregoing, the process for producing carbamates and the process for producing isocyanates have been discussed. However, the production process of the present invention may include known steps, such as pre-treatment steps including a dehydration step; intermediate steps; or post-treatment steps including a purification step and a recovery step.

In the process for producing isocyanates, since the carbamates obtained at a high yield by suppressing the loss of the urea and/or the N-unsubstituted carbamate are thermally decomposed, the yield of the isocyanates can be improved.

EXAMPLES

While in the following, the present invention will be described in further detail with reference to Examples, the present invention is not limited to any of them. In the following description, the units "part(s)" and "%" are by mass, unless otherwise noted.

Example 1

A 300-mL four-neck flask equipped with a condenser was charged with 3.48 parts of zinc hydroxide and 95.0 parts of 1-butanol, and was heated up to 100° C. while stirring. The flask was then charged with a solution in which 13.3 parts of p-toluenesulfonic acid monohydrate was dissolved in 65.0 parts of 1-butanol using a dropping funnel under atmospheric pressure, and the charged mixture was stirred at 100° C. for 10 minutes under atmospheric pressure. Subsequently, the resulting mixture was cooled to room temperature and filtered to give 174.3 parts of a 1-butanol solution containing zinc p-toluenesulfonate.

The 1-butanol solution of zinc p-toluenesulfonate thus obtained above was depressurized at a temperature of 60° C. or lower to remove 1-butanol, so that 15.1 parts of a white solid was obtained.

As a result of analysis, the white solid was found to be a mixture of 80% of zinc p-toluenesulfonate anhydrate and 20% of zinc p-toluenesulfonate hexahydrate. The yield of the zinc p-toluenesulfonate was found to be 96% by mol based on the p-toluenesulfonic acid monohydrate.

The analysis was carried out by element analysis and thermogravimetric analysis in the same manner as described in the above Non-Patent Document 1 (the same applies to the following Examples and Comparative Examples).

Example 2

The same procedures as in Example 1 were carried out except that 4.13 parts by weight of basic zinc carbonate was used instead of 3.48 parts of zinc hydroxide and the stirring time was set to 2 hours, so that a white solid was obtained.

As a result of analysis, the white solid was found to be a mixture of 85% of zinc p-toluenesulfonate anhydrate and 15% of zinc p-toluenesulfonate hexahydrate. The yield of the zinc p-toluenesulfonate was found to be 97% by mol based on the p-toluenesulfonic acid monohydrate.

Further, the white solid was measured by $^1$H-NMR, and the content of the 1-butanol was found to be 4% by weight of the total amount of the zinc toluenesulfonate.

Example 3

The same procedures as in Example 1 were carried out except that 1-octanol was used instead of 1-butanol, so that a white solid was obtained.

As a result of analysis, the white solid was found to be a mixture of 85% of zinc p-toluenesulfonate anhydrate and 15% of zinc p-toluenesulfonate hexahydrate. The yield of the zinc p-toluenesulfonate was found to be 96% by mol based on the p-toluenesulfonic acid monohydrate.

Example 4

The same procedures as in Example 1 were carried out except that the reaction temperature was set to 70° C., so that a white solid was obtained.

As a result of analysis, the white solid was found to be a mixture of 80% of zinc p-toluenesulfonate anhydrate and 20% of zinc p-toluenesulfonate hexahydrate. The yield of the zinc p-toluenesulfonate was 86% by mol based on the p-toluenesulfonic acid monohydrate.

Comparative Example 1

The same procedures as in Example 1 were carried out except that 4.39 parts by weight of zinc carbonate was used instead of 3.48 parts of zinc hydroxide and water was used instead of 1-butanol, so that a white solid was obtained.

As a result of analysis, the white solid was found to be 100% zinc p-toluenesulfonate hexahydrate and no zinc p-toluenesulfonate anhydrate was produced therein. The yield of the zinc p-toluenesulfonate was found to be 97% by mol based on the p-toluenesulfonic acid monohydrate.

Comparative Example 2

The same procedures as in Example 1 were carried out except that 4.39 parts by weight of zinc carbonate was used instead of 3.48 parts of zinc hydroxide and the stirring time was set to 2 hours, so that a white solid was obtained.

As a result of analysis, the white solid was found to be a mixture of 87% of zinc p-toluenesulfonate anhydrate and 13% of zinc p-toluenesulfonate hexahydrate. The yield of the zinc p-toluenesulfonate was 80% by mol based on the p-toluenesulfonic acid monohydrate.

Comparative Example 3

The same procedures as in Example 1 were carried out except that the temperature was set to 60° C., so that a white solid was obtained.

As a result of analysis, the white solid was found to be a mixture of 81% of zinc p-toluenesulfonate zerohydrate and 19% of zinc p-toluenesulfonate hexahydrate. The yield of the zinc p-toluenesulfonate was 18% by mol based on the p-toluenesulfonic acid monohydrate.

Comparative Example 4

The same procedures as in Example 1 were carried out except that water was used instead of 1-butanol, so that a white solid was obtained.

As a result of analysis, the white solid was found to be 100% zinc p-toluenesulfonate hexahydrate and no zinc p-toluenesulfonate anhydrate was produced therein. The yield of the zinc p-toluenesulfonate was found to be 98% by mol based on the p-toluenesulfonic acid monohydrate.

The reaction conditions in Examples and Comparative Examples, the yields of the zinc toluenesulfonate obtained in Examples and Comparative Examples, and the content ratio of the hydrate (on a mass basis) are shown in Table 1.

TABLE 1

|  | Examples | | | |
| --- | --- | --- | --- | --- |
|  | 1 | 2 | 3 | 4 |
| Zinc Compound | Zinc Hydroxide | Basic Zinc Carbonate | Zinc Hydroxide | Zinc Hydroxide |
| Solvent | 1-Butanol | 1-Butanol | 1-Octanol | 1-Butanol |
| Reaction Temperature (° C.) | 100 | 100 | 100 | 70 |
| Evaluation Yield of Zinc Toluenesulfonate (mol %) | 96 | 97 | 96 | 86 |
| Proportion Anhydrate (% by mass) | 80 | 85 | 85 | 80 |
| of Hydrate Hexahydrate (% by mass) | 20 | 15 | 15 | 20 |

|  | Comparative Examples | | | |
| --- | --- | --- | --- | --- |
|  | 1 | 2 | 3 | 4 |
| Zinc Compound | Zinc Carbonate | Zinc Carbonate | Zinc Hydroxide | Zinc Hydroxide |
| Solvent | Water | 1-Butanol | 1-Butanol | Water |
| Reaction Temperature (° C.) | 100 | 100 | 60 | 100 |
| Evaluation Yield of Zinc Toluenesulfonate (mol %) | 97 | 80 | 18 | 98 |
| Proportion Anhydrate (% by mass) | 0 | 87 | 81 | 0 |
| of Hydrate Hexahydrate (% by mass) | 100 | 13 | 19 | 100 |

Example 6

A 1-liter SUS autoclave equipped with a pressure control valve, a reflux condenser, a gas-liquid separator, and a stirrer was charged with a mixture of 2,4-diaminotoluene (76.5 g: 0.626 mol), urea (113 g: 1.87 mol), and 1-butanol (255 g: 3.44 mol), and further charged with the mixture of zinc p-toluenesulfonate (containing anhydrate and hexahydrate) (1.35 g:

3.14 mmol) and 1-butanol (23.4 g: 316 mmol) obtained in Example 1 as a catalyst. While a nitrogen gas was allowed to flow at 1 liter per minute and stirred at 500 rpm, the charged mixture was allowed to react for 4 hours while the internal pressure was controlled with the pressure control valve so that the reaction temperature was maintained at 215° C.

When a portion of the reaction solution was sampled and quantified, it was confirmed that 2,4-bis(butyloxycarbonylamino)toluene was produced at a yield of 83% by mol based on 2,4-diaminotoluene. It was also confirmed that mono(butyloxycarbonylamino)aminotoluene was produced at a yield of 8% by mol.

While the illustrative embodiments of the present invention are provided in the above description, such is for illustrative purpose only and it is not to be construed restrictively. Modification and variation of the present invention that will be obvious to those skilled in the art is to be covered by the following claims.

INDUSTRIAL APPLICABILITY

The process for producing zinc toluenesulfonate according to the present invention can be used for industrial production of zinc toluenesulfonate. The zinc toluenesulfonate of the present invention can be used as a catalyst in various chemical reactions such as a reaction which produces carbamates. Further, the process for producing carbamates according to the present invention can be used for industrial production of carbamates.

The invention claimed is:

1. A process for producing zinc toluenesulfonate, comprising
   allowing a zinc compound comprising $Zn(OH)_2$, and toluenesulfonic acid and/or a salt thereof to react at a temperature higher than 60° C. in the presence of an alcohol having 1 to 20 total carbon atoms.

2. A catalyst in production of carbamates in which aromatic diamine, urea and/or N-unsubstituted carbamate, and alcohol are allowed to react, comprising zinc toluenesulfonate produced by allowing a zinc compound comprising $Zn(OH)_2$, and toluenesulfonic acid and/or a salt thereof to react at a temperature higher than 60° C. in the presence of an alcohol having 1 to 20 total carbon atoms.

3. A catalyst in production of carbamates in which aromatic diamine, urea and/or N-unsubstituted carbamate, and alcohol are allowed to react, comprising zinc toluenesulfonate comprising alcohol in the proportion of not less than 5 ppm to a total amount of zerohydrate to hexahydrate of zinc toluenesulfonate.

4. A process for producing carbamates, comprising:
   allowing aromatic diamine, urea and/or N-unsubstituted carbamate, and alcohol to react in the presence of a catalyst comprising a zinc toluenesulfonate produced by allowing a zinc compound comprising $Zn(OH)_2$, and toluenesulfonic acid and/or a salt thereof to react at a temperature higher than 60° C. in the presence of an alcohol having 1 to 20 total carbon atoms.

5. A process for producing carbamates, comprising:
   allowing aromatic diamine, urea and/or N-unsubstituted carbamate, and alcohol to react in the presence of a catalyst comprising the zinc toluenesulfonate comprising an alcohol in a proportion of not less than 5 ppm to a total amount of zerohydrate to hexahydrate of zinc toluenesulfonate.

* * * * *